United States Patent [19]

Cozad, deceased

[11] Patent Number: 5,049,150
[45] Date of Patent: Sep. 17, 1991

[54] TOOL FOR GRIPPING A BONE FRAGMENT

[75] Inventor: Trent E. Cozad, deceased, late of Fort Wayne, Ind., by Kay M. Cozad, heir

[73] Assignee: Zimmer, Inc., Warsaw, Ind.

[21] Appl. No.: 634,674

[22] Filed: Dec. 27, 1990

[51] Int. Cl.⁵ .............................................. A61F 5/00
[52] U.S. Cl. ........................................ 606/86; 606/96
[58] Field of Search ...................... 606/79, 80, 84, 86, 606/96, 104

[56] References Cited

U.S. PATENT DOCUMENTS 3,892,232  7/1975  Nuefeld ................................ 606/96

OTHER PUBLICATIONS

Zimmer, Inc.—Catalog Illustration 1987—Fermoal Head Extractor.
Zimmer, Inc.—Catalog Illustration 1987—Towel Clamp.

*Primary Examiner*—David J. Isabella
*Assistant Examiner*—Debra S. Brittingham
*Attorney, Agent, or Firm*—Paul David Schoenle

[57] ABSTRACT

A tool for gripping a bone fragment is provided. A first member is engaged with the bone fragment while a second member is carried by the first member to prevent rotation of the bone fragment.

4 Claims, 1 Drawing Sheet

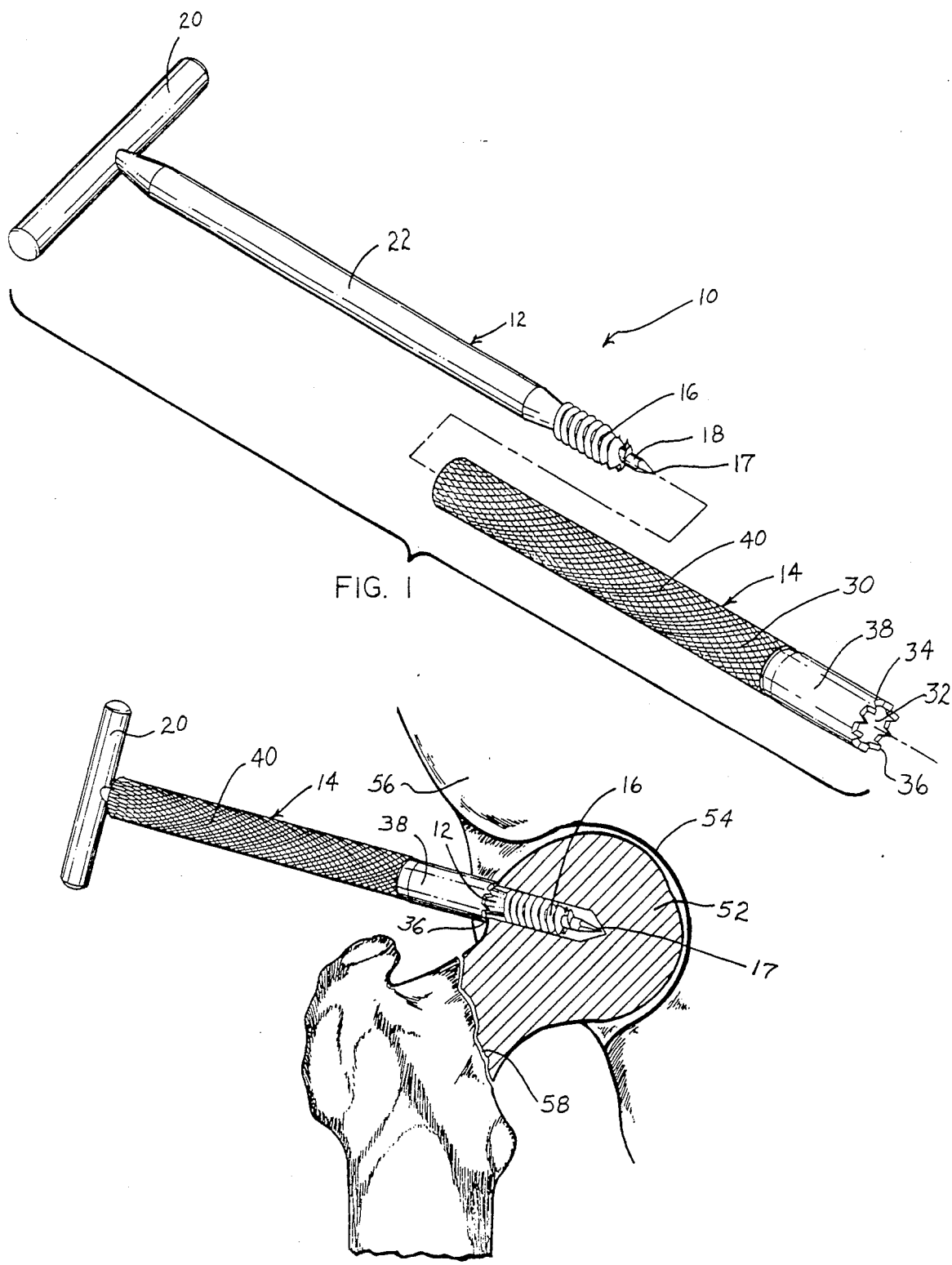

TOOL FOR GRIPPING A BONE FRAGMENT

BACKGROUND OF THE INVENTION

In certain surgical proceedings, it is required to resect a femoral head and remove the latter from its position within the acetabulum. Alternatively, a neck fracture may result in replacement of the femoral head so that removal of the latter is required. Surgeons currently utilize a threaded T-bar with a handle on one end and threads on the other end to engage the femoral head. When the threaded T-bar is rotated to engage the threads with the femoral head, there is a tendency for the femoral head to also rotate so that the surgeon must hold the femoral head to prevent its rotation. This procedure is cumbersome and could lead to sharp bone fragments cutting into the surgeon's gloves and skin. Consequently, it is desirable to provide a safe and easy tool for removal of the femoral head.

SUMMARY OF THE INVENTION

The present invention provides a tool for gripping a bone fragment comprising a first member with means for engaging the bone fragment and a second member with means for engaging the bone fragment, and the second member being movable relative to the first member and cooperating with the bone fragment to oppose movement of the latter while the first member is engaging the bone fragment.

It is an object of the invention to provide a simple two piece tool which is easily manipulated by the surgeon when a femoral head is to be removed from the acetabulum following separation of the femoral head from the femur.

BRIEF DESCRIPTION OF THE DRAWINGS

FIG. 1 is an exploded view of the tool of the present invention; and

FIG. 2 is a view of the tool in engagement with a femoral head.

DETAILED DESCRIPTION

The tool 10 of FIG. 1 includes a first member 12 and a second member 14. The first member 12 forms a self-tapping thread 16 at a leading end 18 and a handle 20 opposite from the leading end 18. The threaded end forms a small portion of the length of the first member while a large portion of the length designated 22 defines a smooth outer surface without threads or interruptions.

The second member 14 forms a cylindrical sleeve 30 with a bore 32 extending therethrough. A leading end 34 of the second member 14 is provided with a plurality teeth 36 that extend axially outward for a purpose to be described hereinafter. A smooth outer surface 38 extends away from the teeth 36 to a knurled outer surface 40 which covers a major portion of the length of the second member 14.

As shown in FIG. 2, the second member 14 fits over the threaded end 16 and the smooth surface portion 22 (not shown). The handle 20 forms a stop to limit movement of the second member 14 away from the threaded end 16. When the second member 14 abuts the handle 20, the threaded end 16 extends outwardly from the second member 14 to expose the self-tapping threads.

A hip joint is illustrated in FIG. 2 with a femoral head 52 disposed within the socket 54 of an acetabulum 56. The femoral head 52 is illustrated with a fractured neck at 58 separating the femoral head from the remaining portion of the femur. If the surgeon decides to remove the femoral head 52 in order to implant a femoral hip stem within the intramedullary cavity of the femur, it will be necessary to remove the femoral head 52 from the acetabulum 56. The surgeon places the tip 17 of the threaded end 18 against the femoral head and pushes against the femoral head toward the pocket 54. At the same time the second member 14 is pushed toward the femoral head to engage the teeth with the femoral head 52. With one hand on the knurled surface 40 and the other hand on the handle 20 it is possible to rotate the first member 12 relative to the second member and femoral head to screw the first member into the femoral head. The one hand and second member cooperate to prevent rotation of the femoral head. With the threaded end 16 engaging the femoral head it is possible to manipulate the latter with the first member 12 to remove the femoral head from the acetabulum.

The smooth surface 38 adjacent the teeth 36 is provided so that debris and body fluid easily wiped off of the second member leading end adjacent the femoral head 52.

What is claimed is:

1. An orthopaedic extractor for removing a bone fragment from a main bone mass comprising a first member including threads at one end for engaging the fragment and an enlarged integral handle on an opposite end the threads to permit turning of the threads into the fragment and manipulation of the fragment away from the main bone mass once it is engaged; and a second tubular member configured for movably carrying the first member, the second member including teeth at one end for engaging the bone fragment and preventing rotation of the fragment and defining a length such that when an opposite end of said second member abuts the handle, the length of the tube does not extend past the threaded and of the first member; whereby the second member prevents rotation of the bone fragment while the first member is threaded into the bone fragment.

2. The tool of claim 1 in which the first member means is defined by a threaded end for engagement with the bone fragments and the first member includes a handle opposite from the threaded end and the second member means is defined by teeth at one end for engagement with the bone fragments.

3. The tool of claim 2 in which the second member is further provided with a knurled surface opposite the one end.

4. The tool of claim 3 in which the second member defines a smooth surface separating the teeth from the knurled surface in order to space the knurled surface from the bone fragments.

* * * * *